(12) United States Patent
Clark

(10) Patent No.: US 6,329,408 B1
(45) Date of Patent: Dec. 11, 2001

(54) HYPOGLYCEMIC THIAZOLIDINEDIONES AND INTERMEDIATES

(75) Inventor: David A. Clark, East Lyme, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 08/458,071

(22) Filed: Jun. 1, 1995

Related U.S. Application Data

(62) Division of application No. 08/162,027, filed on Dec. 1, 1993, now abandoned, which is a continuation of application No. PCT/US92/05436, filed on Jul. 1, 1992, which is a continuation of application No. 07/733,771, filed on Jul. 22, 1991, now abandoned.

(51) Int. Cl.$^7$ ........................ A61K 31/421; C07D 263/32
(52) U.S. Cl. ............................ 514/374; 548/235
(58) Field of Search .............................. 548/235; 514/374

(56) References Cited

U.S. PATENT DOCUMENTS

| | | | |
|---|---|---|---|
| 4,340,605 | 7/1982 | Kawamatsu | 514/342 |
| 4,342,771 | 8/1982 | Schnur | 435/188 |
| 4,367,234 | 1/1983 | Schnur | 424/272 |
| 4,617,312 | 10/1986 | Schnur | 514/369 |
| 4,703,052 | 10/1987 | Eggler | 514/337 |
| 5,036,079 | 7/1991 | Clark | 514/333 |
| 5,089,514 | 2/1992 | Hulin | 514/374 |

FOREIGN PATENT DOCUMENTS 0177353   9/1986   (EP) .

OTHER PUBLICATIONS

Fluka Chiral Compounds. Chemistry p. 148 1995.*
Pyne, S. et al., *J. Am. Chem. Soc.*, 1982, 104, 5728–5740.
Schonenberger, B. et al., *Helvetica Chimica Acta*, 1986, 69, 283–287.
Schonenberger, B. et al., *Helvetica Chimica Acta,*, 1986, 69, 1486–1497.
Meese, C. et al., *Liebigs Ann. Chem.*, 1986, 2004–2007.
Iwata, C. et al., *Chem. Pharm. Bull.*, 1987, 35, 544–552.
Ross & Glomset , New England Journal of Medicine, 1976, 295, 369–77.
Sohda et al., Chemical & Pharmaceutical Bulletin, Japan, 1982, 30, 3580–3600.

* cited by examiner

*Primary Examiner*—Joseph K. McKane
*Assistant Examiner*—Andrea D'Souza
(74) *Attorney, Agent, or Firm*—Peter C. Richardson; Gregg C. Benson; Robert T. Ronau

(57) ABSTRACT

Optically pure thiazolidinedione alcohols and ethers, and synthetic intermediates for preparing said alcohols and ethers. These compounds have utility as hypoglycemic and hypocholesterolemic agents.

15 Claims, No Drawings

HYPOGLYCEMIC THIAZOLIDINEDIONES AND INTERMEDIATES

This is a division of application Ser. No. 08/162,027, filed on Dec. 1, 1993, abandoned, entitled "Hypoglycemic Thiazolidinediones and Intermediates"; which is a continuation of International Application Number PCT/US92/05436, filed Jul. 1, 1992, which is a continuation of U.S. Ser. No. 07/733,771, filed Jul. 22, 1991, abandoned.

BACKGROUND OF THE INVENTION

The present invention relates to certain compounds of formulas I, II and IV, depicted below, having utility as hypoglycemic and hypocholesterolemic agents, methods for their use and pharmaceutical compositions containing them.

In spite of the early discovery of insulin and its subsequent wide-spread use in the treatment of diabetes, and the later discovery and use of sulfonylureas (e.g. chlorpropamide, tolbutamide, acetohexamide, tolazamide) and biguanides (e.g. phenformin) as oral hypoglycemic agents, the treatment of diabetes remains less than satisfactory. The use of insulin, necessary in about 10% of diabetic patients in which synthetic hypoglycemic agents are not effective (Type I diabetes, insulin dependent diabetes mellitus), requires multiple daily doses, usually by self injection. Determination of the proper dosage of insulin requires frequent estimations of the sugar in the urine or in the blood. The administration of an excess dose of insulin causes hypoglycemia, with effects ranging from mild abnormalities in blood glucose or coma, or even death. Treatment of non-insulin dependent diabetes mellitus (Type II diabetes) usually consists of a combination of diet, exercise, oral agents, e.g., sulfonylureas, and in more severe cases, insulin. However, the clinically available hypoglycemics are unfortunately fraught with other toxic manifestations which limit their use. In any event, where one of these agents may fail in an individual case, another may succeed. A continuing need for hypoglycemic agents, which may be less toxic or succeed where others fail, is clearly evident.

Furthermore, atherosclerosis, a disease of the arteries, is recognized to be the leading cause of death in the United States and Western Europe. The pathological sequence leading to atherosclerosis and occlusive heart disease has been described in detail by Ross and Glomset in New England Journal of Medicine 295, 369–377 (1976). The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Cholesterol and cholesteryl ester account for most of this lipid. Further, it is postulated that most of the cholesterol found within the fatty streaks results from uptake from the plasma. These fatty streaks, in turn, give rise to development of the "fibrous plaque", which consists of accumulated intimal smooth muscle cells laden with lipid and surrounded by extra cellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and Is likely in time to become calcified and necrotic, advancing to the "complicated lesion" which accounts for the arterial occlusion and tendency toward mural thrombosis and arterial muscular spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at high risk for development or progression of CVD because of this factor. Individuals who possess independent risk factors in addition to hyperlipidemia are at particularly high risk. Such independent risk factors include glucose intolerance, left ventricular hypertrophy hypertension, and being of the male sex. Cardiovascular disease is especially prevalent among diabetic subjects, at least in part because of the existence of multiple independent risk factors. Successful treatment of hyperlipidemia in the general population, and in diabetic subjects in particular, is therefore of exceptional medical importance.

The first step in recommended therapeutic regimens for hyperlipidemia is dietary intervention. While diet alone produces adequate response In some Individuals, many others remain at high risk and must be treated further by pharmacological means. New drugs for the treatment of hyperlipidemia are, therefore, of great potential benefit for large numbers of individuals at high risk of developing CVD. Further, successful treatment of both the hyperlipidemia and hyperglycemia associated with the diabetic state with a single therapeutic agent is particularly desirable.

In addition to the hypoglycemic agents cited above, a variety of other compounds have been reported to possess this type of activity, as reviewed by Blank [Burger's Medicinal Chemistry, Fourth Edition, Part II, John Wiley and Sons, N.Y. (1979), pp. 1057–1080].

Schnur, U.S. Pat. No. 4,367,234 discloses hypoglycemic oxazolidinediones of the formula

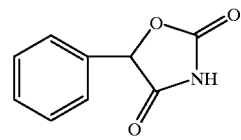

in which the phenyl ring is generally mono- or multi-substituted in the ortho/meta positions. Notably, with the exception of the 4-fluorophenyl analog, the parasubstituted derivatives are either inactive or possess a low level of hypoglycemic activity.

Schnur, U.S. Pat. No. 4,342,771 discloses oxazolidinedione hypoglycemic agents of the formula

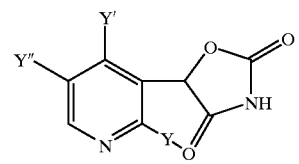

in which Y is hydrogen or alkoxy, Y' is hydrogen or alkyl and Y" is hydrogen or halo.

Schnur, U.S. Pat. No. 4,617,312 discloses hypoglycemic thiazolidinediones of the formula

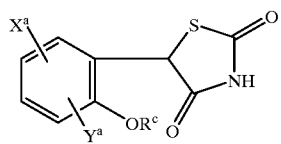

where $R^c$ is lower alkyl, $X^a$ is F, Cl or Br, and $Y^a$ is hydrogen, chloro, lower alkyl or lower alkoxy. Notably, the compounds require ortho-substitution with an alkoxy group, and para-substitution is limited to hydrogen or halogen.

Kawamatsu et al., U.S. Pat. No. 4,340,605, disclose hypoglycemic compounds of the formula

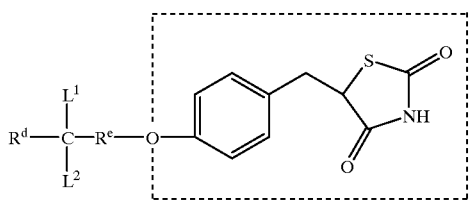

wherein $R^e$ is a bond or lower alkylene and when $R^d$ is an optionally substituted five- or six-membered heterocyclic group including one or two hetero-atoms selected from N, O and S, $L^1$ and $L^2$ may each be defined as hydrogen. Based on a lack of hypoglycemic and plasma triglyceride lowering activity of certain non-ether analogs, it has been suggested that the boxed portion of the structural formula, including the ether oxygen, represents an essential feature for useful activity in this series of compounds; Sohda et al., Chem. Pharm. Bull., Japan, Vol. 30, pp. 3580–3600 (1982).

Eggler et al., U.S. Pat. No. 4,703,052, disclose hypoglycemic thiazolidinediones of the formula

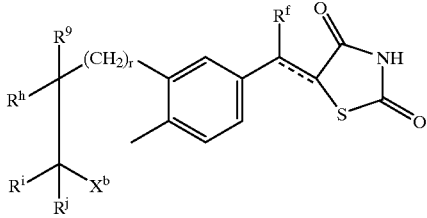

where the dotted line represents an optional bond, $R^f$ is H, methyl or ethyl, $X^b$ is O, S, SO, $SO_2$, $CH_2$, CO, CHOH or $NR^k$, $R^k$ is H or an acyl group and the numerous definitions of $R^g$, $R^h$, $R^i$ and $R^j$ include $R^g$, $R^h$, and $R^i$ as hydrogen or methyl and $R^j$ as optionally substituted phenyl, benzyl, phenethyl or styryl.

Clark, et al., International Patent Publication No. WO 89/08651, disclose hypoglycemic thiazolidinediones of the formula,

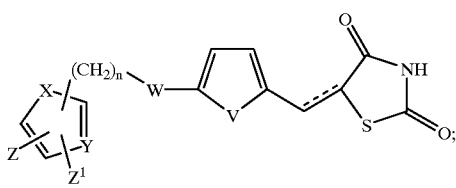

wherein
the dotted line represents a bond or no bond;
V is —CH═CH—, —N═CH—, —CH═N— or S;
W is $CH_2$, CHOH, CO, —C═NOR or —CH═CH—;
X is S, O, $NR^1$, —CH═N— or —N═CH—;
Y is CH or N;
Z is hydrogen, $(C_1-C_7)$alkyl or $(C_3-C_7)$cycloalkyl, phenyl, naphthyl, pyridyl, furyl, thienyl or phenyl mono- or disubstituted with the same or different groups which are $(C_1-C_3)$alkyl, trifluoromethyl, $(C_1-C_3)$alkoxy, fluoro, chloro or bromo;
$Z^1$ is hydrogen or $(C_1-C_3)$alkyl;
R and $R^1$ are each independently hydrogen or methyl; and
n is 1, 2 or 3.

SUMMARY OF THE INVENTION

It is the purpose of the present invention to provide optically pure forms of the alcohol which had previously been disclosed only in its racemic form in the foregoing reference. This invention provides each alcohol in a form essentially free of its corresponding enantiomer.

The present invention is directed to (1S)-5-[4-(3-(5-methyl-2-phenyl-4-oxazolyl)-1-hydroxypropyl)benzyl]thiazolidine-2,4-dione (I), wherein the compound is substantially free of its corresponding 1R enantiomer.

I

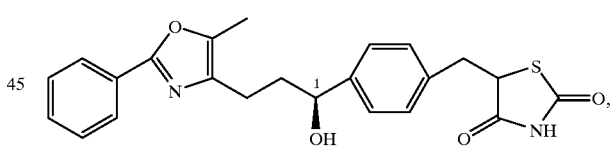

Also embraced by the invention is said 1R enantiomer, (1R)-5-[4-(3-(5-methyl-2-phenyl-4-oxazolyl)-1-hydroxypropyl)benzyl]thiazolidine-2,4-dione (II), wherein said 1R enantiomer is substantially free of its corresponding 1S enantiomer.

II

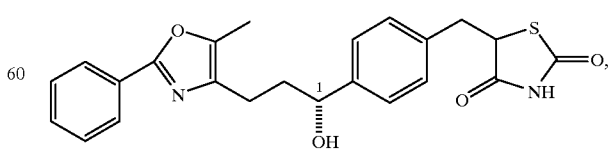

Also included within the scope of the invention are compounds of formula IV,

IV

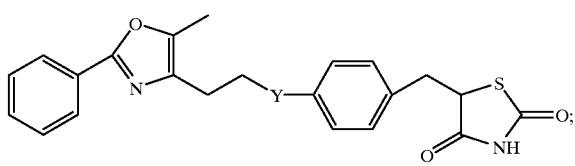

wherein Y is CHOR (racemic),

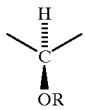

(and essentially free of its corresponding R isomer) or

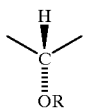

(and essentially free of its corresponding S enantiomer); R is $(C_1-C_4)$alkyl, $(C_7-C_9)$phenylalkyl, phenyl or alkoxyalkyl of the formula $(CH_2)_nO(CH_2)_mCH_3$; n is 2, 3 or 4; m is 0, 1, 2, 3 or 4.

The present invention also embraces pharmaceutically acceptable cationic salts and pharmaceutically acceptable acid addition salts of the compounds of the preceding two paragraphs.

The expression "pharmaceutically-acceptable cationic salt" is intended to define but not limited to such salts as the alkali metal salts, (e.g. sodium and potassium), alkaline earth metal salts (e.g. calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine) diethylamine, piperazine, tromethamine (2-amino-2-hydroxymethyl-1,3-propanediol) and procaine. An especially preferred such salt is the sodium salt.

The expression "pharmaceutically-acceptable acid addition salts" is intended to define but not limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

Also embraced by the present invention are pharmaceutical compositions for use in treating a hyperglycemic mammal or a hypercholesterolemic mammal which comprises a blood glucose lowering amount or a blood cholesterol lowering amount of a compound of formulas I, II and IV and a pharmaceutically-acceptable carrier. The invention further comprises a method of lowering blood glucose in a hyperglycemic mammal which comprises administering to said mammal a blood glucose lowering effective amount of a compound of formulas I, II and IV; and a method of lowering blood cholesterol in a hypercholesterolemic mammal which comprises administering to said mammal a blood cholesterol lowering amount of a compound of the formulas I, II and IV.

Also embraced by the present invention are the key intermediates of formula III,

III

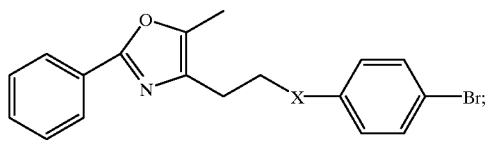

wherein X is

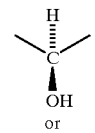

or

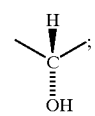

and said intermediate is substantially free of its corresponding enantiomer.

Additional intermediates which are included within the scope of this invention are compounds of formula V,

V

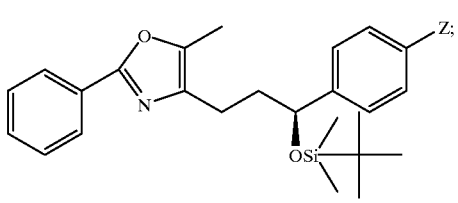

wherein Z is Br,

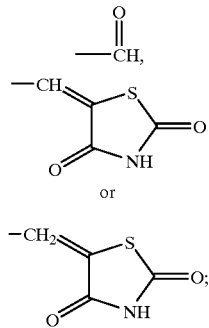

and said intermediate is substantially free of its corresponding enantiomer.

DETAILED DESCRIPTION OF THE INVENTION

All of the compounds described herein are readily prepared according to the reaction sequence depicted in Scheme I and description below.

p-Bromoacetophenone is reacted with sodium hydride and diethylcarbamate in tetrahydrofuran to afford the β-ketoester, which is further reacted with sodium hydride and 5-methyl-2-phenyl-4-oxazolymethyl chloride in tetrahydrofuran followed by hydrolysis and decarboxylation in a refluxing solution of acetic acid and hydrochloric acid to afford the ketone of formula VI.

VI

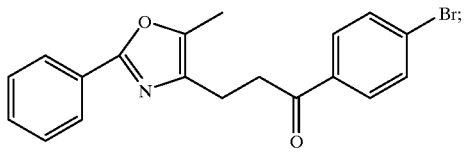

This ketone is converted to its S- and R-alcohol reduction products via one of two separate methods. Thus, reduction of ketone (VI) with sodium borohydride at 0° C. in a solution of tetrahydrofuran and ethanol for about 20 minutes to 8 hours yields the racemic alcohol, which is an equal mixture of the compounds of formulas I and II.

The racemic mixture thus obtained is resolved into its individual optically pure components by reaction with a chiral isocyanate, said chiral isocyanate being chosen for its ability to produce diastereoisomers which are easily separable by some physical means. Thus, (R)-(−)-1-(naphthyl) ethylisocyanate is reacted with the racemic alcohol in refluxing toluene for 17 hours. An additional amount of isocyanate is added, in order to drive the reaction to completion, and reflux is continued for 24 hours. The reaction yields two diastereomeric carbamates of the configurations RR and RS. The differing physical properties of these diastereomers results in one, the RR isomer, being selectively crystallized from a solution containing equal amounts of the two compounds. The solution used in this particular instance is a diethyl ether/hexane (1/2) system. The solid material obtained from this crystallization is recrystallized from ethyl acetate to further purify the (RR)-diastereomer.

The mother liquors of the crystallization and recrystallization steps now predominantly contain the (RS)-diastereomer. Removal of the solvents and purification of the residue on silica gel, eluting with hexane/diethyl ether (1/2) affords the optically pure (RS)-diastereomer.

The diastereomers thus separated are now converted back to the alcohols from the carbamates by reaction of said carbamates with trichlorosilane and triethylamine in benzene. Each of the alcohols thus obtained exist as one enantiomer, substantially free of its corresponding enantiomer.

A second method of obtaining these alcohols is to prepare them in optically pure form directly from the ketone precursor via a stereoselective reduction process, thus eliminating the need for the chiral resolution process. This stereoselective reduction is achieved with a borane reducing agent such as borane methyl sulfide complex, catecholborane or borane tetrahydrofuran in the presence of the appropriate chiral oxazaborolidine catalyst in a cyclic ether solvent such as dioxane or tetrahydrofuran. The choice of the stereochemistry of the catalyst directly influences the stereochemical configuration of the product alcohol. Thus, the choice of an R-configured catalyst results in the S-configured alcohol; the choice of an S-configured catalyst results in the R-configured alcohol. Specifically, the preferred system to produce the S-alcohol is reaction of the ketone of formula VI with borane methyl sulfide complex in tetrahydrofuran in the presence of (R)-tetrahydro-1-methyl-3,3-diphenyl-1H,3H-pyrrolo[1,2-c][1,3,2]oxazaborole at room temperature for about 15 minutes to 3 hours; the preferred system to produce the R-alcohol is reaction of the ketone of formula VI with borane methyl sulfide complex in tetrahydrofuran in the presence of (S)-tetrahydro-1-methyl-3,3-diphenyl-1H,3H-pyrrolo[1,2-c][1,3,2]oxazaborole.

These alcohols are further elaborated to thiazolidinedione alcohols and ethers as depicted in Scheme I. All of the reactions described below are equally successful with either the R or the S configured alcohol of formula III.

An alcohol of formula III is reacted with t-butyidimethylsilylchloride and imidazole in dimethylformamide at room temperature overnight to afford the O-protected alcohol. With the alcohol moiety thus protected, the bromide is converted to an aldehyde using the well-known conditions of n-butyllithium at −78° C., cold quenching of the anion with dry dimethylformamide and standard aqueous workup. Standard aqueous workup is defined as diluting the reaction mixture with water and extraction of the resulting aqueous solution with enough organic solvent, usually two or three portions, to remove any organic compounds from the aqueous solution. The organic solvent, generally ethyl acetate, is then removed in vacuo.

The aldehyde thus obtained is condensed with commercially available 2,4-thiazolidinedione using the conventional methods of refluxing ethanol and piperidine catalysis, to obtain the olefin condensation product. The olefin thus generated is hydrogenated by introducing hydrogen into a sealed reaction vessel containing the olefin, a reaction-inert solvent and a catalyst. The pressure Inside the reaction vessel can vary from 15 to 50 PSI. Hydrogenation will occur within about 2 to 48 hours under these conditions. The preferred catalyst is palladium due to its resistance to poisoning by sulfur; and the palladium is supported on an inert substrate such as carbon. By "reaction inert solvent" is meant a solvent which will not decompose or otherwise interfere with the reaction. Reaction inert solvents for reactions of this type-include ethanol, methanol and tetrahydrofuran but are not limited to these solvents. The preferred solvent in this case is tetrahydrofuran.

The protecting group is removed using 3.5% aqueous perchloric acid in tetrahydrofuran at room temperature for about 12 hours. The end result of this reaction is an alcohol of formula I or of formula II. The alcohol thus obtained will depend upon which enantiomeric alcohol was selected after said alcohols were obtained in optically purified form.

The optically pure alcohols of formula III are also useful as intermediates in preparing the ether derivatives of formula IV. Thus, reaction of an alcohol of either formula III with a suitable base and an alkyl, alkoxyalkyl, phenyl or aralkyl halide of the formula RX in a reaction inert solvent at a temperature ranging from 0° C. to the reflux temperature of the particular solvent chosen for 2 to 48 hours. The R portion of the RX compound is $(C_1-C_4)$alkyl, $(C_7-C_9)$ aralkyl, phenyl or alkoxyalkyl of the formula—$(CH_2)_nO(CH_2)_mCH_3$; wherein n is 2, 3 or 4 and m is 0, 1, 2, 3 or 4. The X portion is chloro, bromo or iodo. A reaction inert solvent for reactions of this type include but are not limited to diethylether, dioxane, dimethoxyethane, tetrahydrofuran and dimethylformamide. The preferred solvent is tetrahydrofuran, while the preferred base is sodium hydride. The preferred alkyl halides are methyl iodide, ethyl iodide and benzyl bromide.

The ethers prepared as described in the preceding paragraph are individually converted to thiazolidine-2,4-dines of formula IV in the same manner as recited for preparation of compounds of formulas I and II. Thus, the bromo moiety of the ether of formula III is reacted with n-butyllithium and dimethylformamide in tetrahydrofuran to produce an aldehyde, which is reacted with 2,4-thiazolidinedione and catalytic piperidine in ethanol to produce the condensation product as an olefin. This olefin is hydrogenated in the presence of palladium on carbon in tetrahydrofuran to produce the desired final product of formula IV. The specific details of the reactions used to produce these ethers are analogous to the details described the in the preceding paragraphs in regard to the preparation of alcohols of formulas I and II.

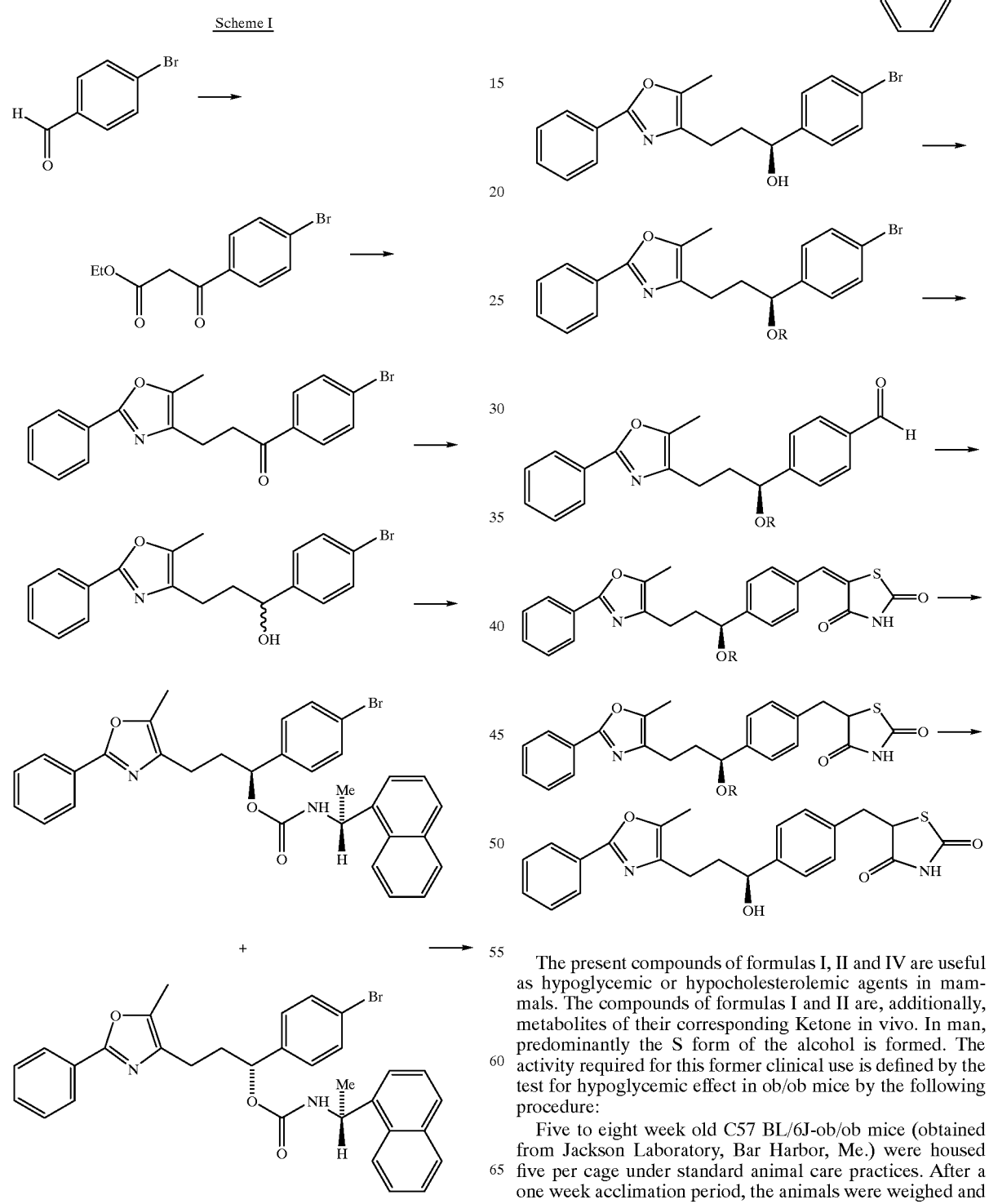

The present compounds of formulas I, II and IV are useful as hypoglycemic or hypocholesterolemic agents in mammals. The compounds of formulas I and II are, additionally, metabolites of their corresponding Ketone in vivo. In man, predominantly the S form of the alcohol is formed. The activity required for this former clinical use is defined by the test for hypoglycemic effect in ob/ob mice by the following procedure:

Five to eight week old C57 BL/6J-ob/ob mice (obtained from Jackson Laboratory, Bar Harbor, Me.) were housed five per cage under standard animal care practices. After a one week acclimation period, the animals were weighed and 25 microliters of blood was collected via an ocular bleed prior to any treatment. The blood sample was immediately diluted 1:5 with saline containing 2.5 mg/ml sodium fluoride and 2% sodium heparin, and held on ice for metabolite analysis. Animals were then dosed daily for five days with drug (5–50 mg/kg), a positive control (50 mg/kg) of ciglitazone; U.S. Pat. No. 4,467,902; Sohda et al., Chem. Pharm. Bull., vol. 32, pp. 4460–4465, 1984), or vehicle. All drugs were administered in a vehicle consisting of 0.25% w/v methyl cellulose. On day 5, the animals were weighed again and bled (via the ocular route) for blood metabolite levels. The freshly collected samples were centrifuged for two minutes at 10,000×g at room temperature. The supernatant was analyzed for glucose, for example, by the ABA 200 Bichromatic Analyzer", using the Agent" glucose UV reagent system (hexokinase method, a modification of the method of Richterich and Dauwalder, Schweizerische Medizinische Wochenschrift, 101, 860 (1971).) using 20, 60 and 100 mg/dl standards. Plasma glucose was then calculated by the equation, Plasma glucose (mg/dl)=Sample value×5×1.67=8.35×Sample value, where 5 is the dilution factor and 1.67 is the plasma hematocrit adjustment (assuming the hematocrit is 40%). "A registered trademark of Abbott Laboratories, Diagnostics Division, 820 Mission Street, So. Pasadena, Calif. 91030.

The animals dosed with vehicle maintain substantially unchanged hyperglycemic glucose levels (e.g., 250 mg/dl), while positive control animals have depressed glucose levels (e.g., 130 mg/dl). Test compounds are reported in terms of % glucose normalization. For example, a glucose level which is the same as the positive control is reported as 100%.

Studies such as that described below demonstrate that the compounds of formula (I) effect the lowering of serum cholesterol levels in mammals.

Female mice (strain C57Br/cd J), obtained from Jackson Laboratories, Bar Harbor, Me., are used at age 8–12 weeks, following 2–4 weeks acclimation having free access to water and standard laboratory chow. Animals are divided randomly into three groups of 6–7 animals. All three groups are placed on a diet containing 0.75% cholesterol, 31% sucrose, 15.5% starch, 20% casein, 17% cellulose, 4.5% corn oil, 5% coconut oil, 0.25% cholic acid, 4% salts and 2% vitamin; permitted to feed ad lib for 18 days; and dosed daily at 9–11 a.m. for the final 5 days by oral gavage, the control group with 5 ml/kg of vehicle (0.1% aqueous methyl cellulose) and the test groups with the compound under study at doses ranging from 0.1 to 10 mg/kg/day in vehicle. After the fourth day of dosing, the animals are fasted overnight, starting at 5 p.m. The following morning a fifth and final dose of the compound is administered to the test groups and, three hours later, the animals are sacrificed by decapitation. Blood from the body trunk is collected and allowed to clot, and the serum assayed enzymatically, using an Abbott VP automated analyzer, for HDL cholesterol, LDL and VLDL cholesterol, and total cholesterol. Whether judged on the basis LDL+VLDL cholesterol levels, total cholesterol levels or the ratio of LDL+VLDL/HDL, the compounds of this invention generally show favorable result in lowering cholesterol levels.

The present compounds of the formulas (I, II and II) can be clinically administered to mammals, including man, via either the oral or the parenteral route. Administration by the oral route is preferred, being more convenient and avoiding the possible pain and irritation of injection. However, in circumstances where the patient cannot swallow the medication,, or absorption following oral administration is impaired, as by disease or other abnormality, it is essential that the drug by administered parenterally. By either route, the dosage is in the range of about 0.10 to about 50 mg/kg body weight of the subject per day, preferably about 0.10 to about 10 mg/kg body weight per day administered singly or as a divided dose. However, the optimum dosage for the individual subject being treated will be determined by the person responsible for treatment, generally smaller doses being administered Initially and thereafter increments made to determine the most suitable dosage. This will vary according to the particular compound employed and with the subject being treated.

The compounds can be used in pharmaceutical preparations containing the compound, or pharmaceutically acceptable acid salt thereof, in combination with a pharmaceutically-acceptable carrier or diluent. Suitable pharmaceutically-acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts of the compounds. The injectable solutions prepared in this manner can then be administered intravenously, intraperitoneally, subcutaneously, or intramuscularly, with intramuscular administration being preferred in man.

The present invention is illustrated by the following Examples. However, it should be understood that the invention is not limited to the specific details of these examples. All reactions are conducted under an inert atmosphere, such as nitrogen, unless otherwise specified. The abbreviations THF and DMF, where used, refer to tetrahydrofuran and dimethylformamide respectively. Such solvents are assumed to contain a small enough water content such that said water does not interfere with the course of the recited reactions. Nomenclature used herein is based on Rigaudy and Klesney, IUPAC Nomenclature of Organic Chemistry, 1979 Ed., Pergamon Press, New York, N.Y., 1979.

EXAMPLE 1

Ethyl 4-Bromobenzoylacetate

Sodium hydride (5.2 g, 0.21 mol) was suspended in dry diethyl ether and cooled to 0° C. Diethyl carbonate (17.7 g, 0.15 mol) was added and the contents were stirred for ten minutes, at which time dropwise addition of p-bromoacetophenone (19.9 g, 0.1 mol) in diethyl ether (50 mL) and ethanol (0.2 mL) was initiated. Addition was continued for twenty minutes; the solution was refluxed for three hours, cooled to room temperature and poured onto cold 10% aqueous hydrochloric acid (250 mL). The aqueous solution was extracted twice with diethyl ether (750 mL) and the combined extracts were washed successively with water (250 mL), brine (250 mL) and dried ($MgSO_4$). The solvent was removed in vacuo and the residue was purified on silica gel, eluting with hexane/ethyl acetate (4/1), to afford 20.2 g (74%) of the title compound as an oil. $^1$HNMR (60MHz, CDCl$_3$): δ1.2 (t,3H), 3.9 (s, 2H), 4.1 (q, 2H), 7.55 (d, J=7 Hz, 2H), 7.75 (d, J=2 Hz, 2H).

EXAMPLE 2

4-[3-(5-Methyl-2-phenyloxazolyl)propionyl]bromobenzene

Sodium hydride (1.3 g, 55 mmol) was suspended in THF (75 mL) and cooled to 0° C. The title compound of Example 1 (14.9 g, 55 mmol) was dissolved in THF (75 mL) and added dropwise to the suspension over 30 minutes. The resulting solution was stirred an additional 30 minutes after which time solid 5-methyl-2-phenyl-4-oxazolyl methyl chloride (10.0 g, 48 mmol) was added in portions over five minutes. The reaction mixture was refluxed for 48 hours, cooled to room temperature and concentrated in vacuo. The residue was dissolved in acetic acid (120 mL) and concentrated HCl (30 mL), and refluxed for five hours. The reaction mixture was cooled to room temperature and poured onto ice-water (300 mL). The aqueous solution was extracted twice with ethyl acetate (500 mL) and the organic extracts were combined and washed with brine (250 mL), dried (MgSO$_4$) and concentrated in vacuo. Purification on silica gel, eluting with hexane/ethyl acetate (4/1), resulted in a crude solid which was further purified by recrystallization from hexane to afford the title compound (11.5 g, 65%) as white crystals. mp 80–81° C. $^1$HNMR (60 MHz, CDCl$_3$): δ2.2 (s, 3H), 2.8 (m, 2H), 3.2 (m, 2H), 7.2–8.0 (m, 9H).

EXAMPLE 3

(S)-4-[3-(5-Methyl-2-phenyl-4-oxazolyl)-1-hydroxypropyl]bromobenzene

The title compound of the preceding example (20 g, 54 mmol) was dissolved in THF (200 mL) at ambient temperature and treated with 4A molecular sieves (10 g, predried under high vacuum at 150° C. overnight). After standing overnight, the solution was decanted from the sieves and was found to have 0.0092% water (by Karl Fisher analysis). (R)-Tetrahydro-1-methyl-3,3-diphenyl-1H,3H-pyrrolo[1,2-c][1,3,2]oxazaborole (748 mg, 2.7 mmol) was added at ambient temperature and the solution was treated with borane methyl sulfide complex (2M in THF, 76 mL, 152 mmol) dropwise over 75 minutes. The reaction mixture was stirred for an additional 15 minutes, cooled to 0OC and quenched by the dropwise addition of methanol (280 mL). The quenched solution was stirred for 18 hours at ambient temperature. The solvents were removed in vacuo and the residue was dissolved In methylene chloride (200 mL) and washed successively with pH 4 aqueous phosphate buffer (200 mL), water (200 mL) and dried (MgSO$_4$). The organic layer was distilled at atmospheric pressure until a volume of 100 mL remained. Hexane was added, and the distillation was continued until the temperature of the distillate reached 62° C. The heat source was removed, and the residue crystallized and granulated over 16 hours. A white solid was collected by vacuum filtration and was dried under high vacuum to afford the title compound (17.46 g, 87%, >99% enantiomeric excess).

EXAMPLE 4

4-[3-(5-Methyl-2-phenyl-4-oxazolyl)-1-hydroxypropyl]bromobenzene

The title compound of Example 2 (5.0 g, 13 mmol) was dissolved in THF (75 mL) and added dropwise over 20 minutes to a suspension of sodium borohydride (513 mg, 13 mmol) in 75 mL of ethanol at 0° C. and the reaction mixture was stirred for 3 hours at 0° C. The reaction mixture was poured onto ice-water (500 mL) and extracted twice with diethyl ether (700 mL). The organic extracts were combined and washed with water (250 mL), brine (250 mL) and dried (MgSO$_4$). The solvent was removed in vacuo and the residue was recrystallized from hexane to afford 4.4 g (92%) of the racemic title compound. mp 82–83° C. $^1$HNMR (60 MHz, CDCl$_3$): δ2.0 (m, 2H), 2.2 (s, 3H), 2.5 (t, J=6 Hz, 2H), 4.6 (m, 1H), 4.7 (broad s, 1H, hydroxyl proton), 7.1–7.5 (m, 7H), 7.8–8.0 (m, 2H).

EXAMPLE 5

(RR)-4-[3-(5-Methyl-2-phenyl-4-oxazolyl)-1-(1-naphthyl)ethylaminocarbonyloxy)propyl]bromobenzene The title compound of Example 4 (1.8 g, 5 mmol) was treated with (R)-(–)-1-(naphthyl)ethylisocyanate (1.0 g, 5 mmol) in toluene (100 mL) and the resulting solution was refluxed for 17 hours. An additional 1 g of the isocyanate was added and reflux was continued for an additional 24 hours. The solvent was removed in vacuo and the residue was crystallized from diethyl ether/hexane (1/2) to afford 1.1 g (37%) of a solid. Recrystallization from ethyl acetate afforded 570 mg (20%) of the pure more polar diastereomeric title compound mp 185–186° C. $[α]_D$–11.97 (C=0.03, DMSO).

EXAMPLE 6

(RS)-4-[3-(5-Methyl-2-phenyl-4-oxazolyl)-3-(1-naphthyl)ethylaminocarbonyloxy)propyl]bromobenzene The mother liquors from the crystallization and recrystallization steps of the preceding example were concentrated in vacuo and purified on silica gel, eluting with hexane/diethyl ether (1/2) to afford 630 mg (22%) of the pure less polar diastereomer. mp 120–125° C. $[α]_D$–39.55 (C=0.31, DMSO).

EXAMPLE 7

(S)-4-[3-(5-Methyl-2-phenyl-4-oxazolyl)-1-hydroxypropyl]bromobenzene

The title compound of Example 6 (1.56 g, 2.7 mmol) was dissolved in benzene (65 mL), treated with trichlorosilane (1.4 mL) and triethylamine (1.9 mL), and the resulting solution was stirred at ambient temperature for 18 hours. The reaction mixture was diluted with water (250 mL) and ethyl acetate (250 mL) and stirred for ten minutes. The layers were separated and the aqueous solution was extracted with ethyl acetate (250 mL). The organic extracts were combined, washed with saturated aqueous sodium bicarbonate (100 mL), water (100 mL), brine (100 mL) and dried (MgSO$_4$). The solvents were removed in vacuo and the residue was purified on silica gel, eluting with hexane/diethyl ether (1/1), to afford the pure S-alcohol as a gum (820 mg, %). The $^1$HNMR was identical to that of the racemic mixture.

EXAMPLE 8

(S)-4-[1-(t-butyldimethylsilyloxy)-3-(5-methyl-2-phenyl)-4-oxazolyl)propyl]bromobenzene The title compound of Example 7 (769 mg, 2.0 mmol), t-butyldimethylsilylchloride (377 mg, 2.5 mmol) and imidazole (340 mg, 5.0 mmol) were combined in DMF (10 mL) and stirred at room temperature for 24 hours. The reaction mixture was diluted with water (100 mL) and extracted with ethyl acetate (2×100 mL). The organic layers were combined, washed with water (100 mL), saturated aqueous sodium bicarbonate (100 mL), brine (100 mL) and dried (MgSO$_4$). The solvent was removed in vacuo to afford the title compound as a gum (860 mg, 85%). $^1$HNMR (60 MHz, CDCl$_3$): δ0.5 (d, 6H), 1.0 (s, 9H), 2.0–2.7 (m, 4H), 2.3 (s, 3H), 4.8 (t, J=5 Hz, 1H), 7.1–7.6 (m, 7H), 7.9–8.1 (m, 2H).

EXAMPLE 9

(S)-4-[1-(t-butyldimethylsilyloxy)-3-(5-Methyl-2-phenyl-4-oxazolyl)propyl]benzaldehyde n-Butyllithium (1.6 M in hexane, 1.3 mL) was added over ten minutes to a cooled (−78° C.) solution of the title compound of Example 8 (780 mg, 1.6 mmol) In THF (60 mL). The reaction mixture was stirred at −78° C. for an additional 50 minutes and dry DMF (152 mg, 2.0 mmol) was added. The reaction mixture was stirred for an additional 1.5 hours at −78° C. and then at room temperature for 1.5 hours. The reaction mixture was diluted with ethyl acetate (200 mL) and washed with water (50 mL), 10% aqueous saturated sodium bicarbonate (50 mL), water (50 mL), brine (50 mL) and dried (MgSO$_4$). The solvent was removed in vacuo and the residue was purified on silica gel, eluting with hexane/diethyl ether (4/1), to afford the title aldehyde (650 mg, 93%). $^1$HNMR (60 MHz, CDCl$_3$): δ0.5 (d, 6H), 1.0 (s, 9H), 2.0–2.7 (m, 4H), 2.3 (s, 3H), 4.9 (dd, J=6 Hz, 12 Hz, 1H), 7.2–8.0 (m, 9H), 10.1 (s, 1H).

EXAMPLE 10

(S)-5-[4-(1-t-butyldimethylsilyloxy)-3-(5-methyl-2-phenyl-4-oxazolyl)propyl)phenylmethylene]thiazolidine-2,4-dione The title compound of Example 9 (341 mg, 0.78 mmol), 2,4-thiazolidinedione (183 mg, 1.56 mmol) and piperidine (14 mg, 0.15 mmol) were combined in ethanol (10 mL) and refluxed for 18 hours. The reaction mixture was cooled to room temperature and concentrated in vacuo. The residue was purified on silica gel, eluting with hexane/-ethyl acetate/acetic acid (16/4/1), to afford a solid which was triturated in hexane to yield the title compound as a white solid (163 mg, 39%). mp 158–160° C. $^1$HNMR (300 MHz, CDCl$_3$): δ−0.5 (d, 6H), 1.0 (s, 9H), 2.0–2.7 (m, 4H), 2.3 (s, 3H), 4.9 7H), 7.8 (s, 1H), 8.0 (m, 2H).

EXAMPLE 11

(S)-5-[4-(1-t-butyldimethylsilyloxy)-3-(5-methyl-2-1-phenyl-4-oxazolyl)propyl)benzyl]thiazolidine-2,4-dione The title compound of Example 10 (160 mg, 0.3 mmol) and 10% palladium on carbon (160 mg) were combined in THF (10 mL) and hydrogenated on a Parr Shaker at 50 PSI and room temperature for 22 hours. The suspension was filtered through diatomaceous earth and the solvent was removed in vacuo to afford the title compound as a gum (180 mg, %). $^1$HNMR (300 MHz, CDCl$_3$): δ0.5 (d, 6H), 1.0 (s, 9H), 2.0–2.2 (m, 2H), 2.3 (s, 3H), 2.4–2.6 (m, 2H), 3.4 (dd, 1H), 4.3 (dd, 1H), 4.7 (dd, 1H), 7.0–7.3 (m, 7H), 7.8 (m, 2H).

EXAMPLE 12

Sodium salt of (S)-5-[4-(3-(5-methyl-2-phenyl-4-oxazolyl)-1-hydroxypropyl)benzyl]thiazolidine-2,4-dione The title compound of Example 11 (160 mg, 0.3 mmol) was dissolved in THF (5 mL) and treated with 3.5% aqueous perchloric acid (3 mL). The reaction mixture was stirred at room temperature for 12 hours, diluted with ethyl acetate (25 mL), washed with water (25 mL), brine (25 mL) and dried (MgSO$_4$). The solvent was removed in vacuo and the residue was purified on silica gel, eluting with hexane/ethyl acetate/acetic acid (66/33/1), to afford 115 mg of the free base as a gum. The gum was dissolved in methanol (10 mL), treated with sodium methoxide (15 mg, 0.3 mmol) and stirred at room temperature for 2.5 hours. The solvent was removed in vacuo and the residue was triturated with diethyl ether to afford the title compound as a solid (79 mg, 60%). mp 235–240° C. $^1$HNMR (300 MHz, DMSO-d$_6$): δ1.9 (m, 2H), 2.3 (s, 3H) 2.5 (m, 2H), 2.7 (dd, 1H), 3.4 (dd, 1H), 4.1 (dd, 1H), 4.5 (m, 1H), 5.2 (d, 1H, hydroxyl proton), 7.1 (d, 2H), 7.5 (m, 3H), 7.9 (m, 2H).

EXAMPLE 13

Sodium salt of (R)-5-[4-(3-(5-Methyl-2-phenyl-4-oxazolyl)-1-hydroxypropyl)benzyl]thiazolidine-2,4-dione By performing substantially the consecutive steps recited in Examples 7–12, beginning with the title compound of Example 5, the title compound of this example was prepared. mp 245–250° C. $^1$HNMR (300 MHz, DMSO-d$_6$): δ1.9 (m, 2H), 2.3 (s, 3H), 2.5 (m, 2H), 2.7 (dd, 1H), 3.4 (dd, 1H), 4.1 (dd, 1H), 4.5 (m, 1H), 5.2 (d, 1H, hydroxyl proton), 7.1 (d, 2H), 7.5 (m, 3H), 7.9 (m, 2H).

EXAMPLE 14

(S)-4-[3-(5-methyl-2-phenyl-4-oxazolyl)-1-ethoxypropyl]bromobenzene

The title compound of Example 7 (1.0 g, 2.7 mmol) and sodium hydride (324 mg, 6.7 mmol) were dissolved in THF (30 mL) at 0° C. The reaction mixture was treated with ethyl iodide (1.0 g, 6.7 mmol) and the contents were refluxed for 18 hours. The reaction mixture was cooled to room temperature and concentrated in vacuo, dissolved in water (25 mL) and extracted twice with ethyl acetate (50 mL). The organic extracts were combined, washed with water (25 mL), brine (25 mL) and dried (MgSO$_4$). The solvent was removed in vacuo and the residue was purified on silica gel, eluting with hexane/ethyl acetate (3/1), to afford the title compound as a gum (1.1 g, 90%). $^1$HNMR (300 MHz, CDCl$_3$): δ1.15 (t, 3H), 2.0 (m, 2H), 2.3 (s, 3H), 2.5 (t, 2H), 3.2–3.4 (m, 2H) 4.2 (dd, 1H), 7.2 (d, 2H), 7.4 (m, 5H), 7.9 (d, 2H).

EXAMPLE 15

The following optically pure ether derivatives were prepared by reaction of the appropriate alkyl halide (RX) with the requisite optically pure alcohol of the indicated stereochemistry using substantially the same procedure recited in Example 14.

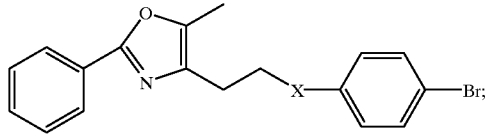

| R | * |
|---|---|
| Me | R |
| Me | S |
| benzyl | S |

EXAMPLE 16

(S)-4-[(5-Methyl-2-phenyl-4-oxazolyl)-1-methoxypropyl]benzaldehyde (S)-4-[3-(5-Methyl-2-phenyl-4-oxazolyl)-3-methoxypropyl]bromobenzene (1.1 g, 2.8 mmol, prepared as described in Example 15) was dissolved in THF (30 mL), cooled to −78° C. and treated with n-butyllithium (2.5 M in THF, 1.2 mL, 3.0 mmol) dropwise via syringe. Following addition, the reaction mixture was stirred at −78° C. for an additional hour and treated with dry DMF (220 mg, 30 mmol). The reaction mixture was stirred at −78° C. for 90 minutes and at ambient temperature for 24 hours. The reaction mixture was diluted with ethyl acetate (200 mL), washed with water (50 mL), 10% aqueous hydrochloric acid (50 mL), water (50 mL), brine (50 mL) and dried (MgSO$_4$). The solvent was removed in vacuo and the residue was purified on silica gel, eluting with hexane/ethyl acetate (3/1), to afford a viscous oil (580 mg, 62%). $^1$HNMR (300 MHz, CDCl$_3$): δ2.0 (m, 2H), 2.3 (s, 3H), 2.5 (t, 2H), 3.2 (s, 3H), 4.15 (dd, 1H), 7.3 (m, 3H), 7.4 (d, 2H), 7.8 (d, 2H), 7.9 (m, 2H), 9.9 (s, 1H).

EXAMPLE 17

(S)-5-[4-(3-(5-methyl-2-phenyl-4-oxazolyl)-1-methoxypropyl)phenylmethylene]thiazolidine-2,4-dione The title compound of Example 16 (580 mg, 1.7 mmol), piperidine (30 mg, 0.34 mmol) and 2,4thiazolidinedione (405 mg, 3.4 mmol) were combined in ethanol (20 mL) and the resulting solution was refluxed overnight. The solvent was removed in vacuo and the residue was purified on silica gel, eluting with hexane/ethyl acetate (3/1) plus 5% acetic acid, to afford the title compound as a solid (640 mg, 87%). mp 205–206° C. $^1$HNMR (300 MHz, DMSO-d$_6$): δ2.0 (m, 2H), 2.3 (s, 3H), 2.4 (t, 2H), 3.1 (s, 3H), 4.2 (dd, 1H), 7.4 (m, 5H), 7.6 (d, 2H), 7.7 (s, 1H), 7.9 (m, 2H).

EXAMPLE 18

(S)-5-[4-(3-(5-Methyl-2-phenyl-4-oxazolyl)-1-methoxypropyl)benzyl]thiazolidine-2,4-dione The title compound of Example 17 (640 mg, 1.5 mmol) was dissolved in THF (50 mL) and hydrogenated in the presence of sulfur-resistant 10% palladium on carbon (640 mg) on a Parr Shaker at 50 PSI for 20 hours. The catalyst was removed via filtration through diatomaceous earth and the filtrate was concentrated in vacuo. The residue was purified on silica gel, eluting with hexane/ethyl acetate (3/1) plus 5% acetic acid, to afford crude material which was further purified by (dissolving the residue in 50 mL of ethyl acetate, washing with water (25 mL), saturated aqueous sodium bicarbonate (25 mL), brine (25 mL) and drying (MgSO$_4$), to afford a colorless gum (229 mg, 35%). $^1$HNMR (300 MHz, CDCl$_3$): δ2.0 (m, 2H), 2.3 (s, 3H), 2.5 (t, 2H), 3.1 (dd, 1H), 3.2 (s, 3H), 3.5 (dd, 1H), 4.1 (dd, 1H), 4.4 (dd, 1H), 7.2 (m, 4H), 7.4 (m, 3H), 7.9 (m, 2H), 8.1 (bs, 1H, NH).

EXAMPLE 19

By performing substantially the consecutive steps recited in Examples 16 through 18 and beginning with an ether prepared as described in Examples 14 and 15, the following ether derivatives were prepared.

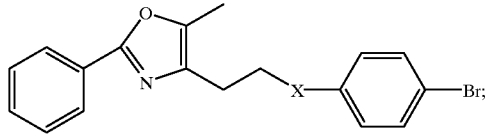

| R | * |
|---|---|
| Me | R |
| Me | S |
| Et | S |
| benzyl | S |

What is claimed is:

1. A compound of formula III,

III

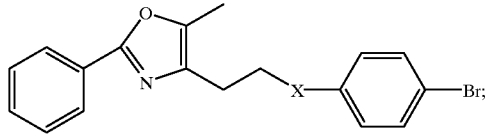

wherein X is

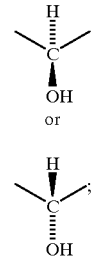

or and said compound being substantially free of its corresponding enantiomer.

2. The compound according to claim 1 wherein X is

3. An oxazole of formula IV,

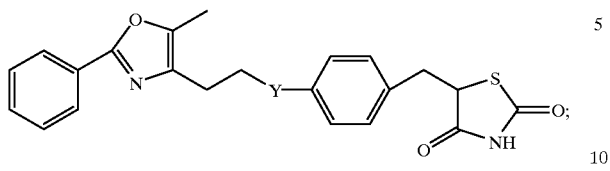

IV wherein Y is CHOR; R is $(C_1-C_4)$alkyl, $(C_7-C_9)$ phenylalkyl, phenyl or alkoxyalkyl of the formula —$(CH_2)_nO(CH_2)_mCH_3$; n is 0, 1, 2, 3 or 4; m is 2, 3 or 4; pharmaceutically acceptable cationic salts thereof; and pharmaceutically acceptable acid addition salts thereof.

4. A compound according to claim 3 wherein Y has the R configuration, said compound being substantially free from the enantiomer in which Y has the S configuration.

5. The compound according to claim 4 wherein R is methyl.

6. The compound according to claim 4 wherein R is ethyl.

7. The compound according to claim 4 wherein R is benzyl.

8. The compound according to claim 3 wherein Y has the S configuration, said compound being substantially free from the enantiomer in which Y has the R configuration and R is methyl.

9. An oxazole of formula V,

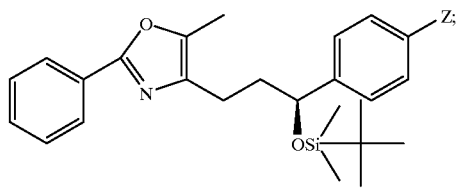

V wherein Z is Br,

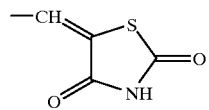

or

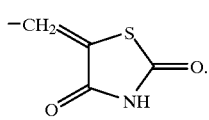

10. The compound according to claim 9 wherein Z is Br.

11. The compound according to claim 9 wherein Z is

12. The compound according to claim 9 wherein Z is

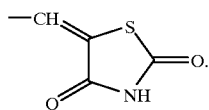

13. The compound according to claim 9 wherein Z is

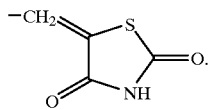

14. A pharmaceutical composition for use in a hyperglycemic or hypercholesterolemic mammal which comprises a blood glucose lowering amount or blood cholesterol lowering amount of a compound of claim 3 and a pharmaceutically acceptable carrier.

15. A method of lowering the blood glucose in a hyperglycemic or hypercholesterolemic mammal which comprises administering to said mammal a blood glucose lowering effective amount or blood cholesterol lowering effective amount of a compound of claim 3.

* * * * *